US006391634B1

(12) United States Patent
Rook et al.

(10) Patent No.: US 6,391,634 B1
(45) Date of Patent: May 21, 2002

(54) MONOCLONAL ANTIBODIES AND THEIR PRODUCTION AND USE

(75) Inventors: Graham Arthur William Rook, Haver Hill; Jennifer Jane Edge, Drayton, both of (GB)

(73) Assignee: G. D. Searle & Co., Chicago, IL (US)

( * ) Notice: Subject to any disclaimer, the term of this patent is extended or adjusted under 35 U.S.C. 154(b) by 0 days.

(21) Appl. No.: 08/031,075

(22) Filed: Mar. 10, 1993

Related U.S. Application Data

(63) Continuation of application No. 07/892,394, filed on May 28, 1992, now abandoned, which is a continuation of application No. 07/510,639, filed on Apr. 18, 1990, now abandoned, which is a continuation of application No. 07/078,770, filed on Jul. 28, 1987, now abandoned.

(30) Foreign Application Priority Data

Jul. 29, 1986 (GB) ............................................. 8618443

(51) Int. Cl.$^7$ ............................. C12N 5/06; C12N 5/16; C12N 5/10; C07K 16/00
(52) U.S. Cl. ..................... 435/340; 435/354; 530/388.4
(58) Field of Search ................... 530/388.4; 435/240.27, 435/172.3, 340, 354

(56) References Cited

U.S. PATENT DOCUMENTS

| 4,292,296 A | | 9/1981 | Parsons, Jr. ..................... 424/1 |
| 4,489,167 A | * | 12/1984 | Ochi et al. ................... 436/518 |
| 4,659,659 A | * | 4/1987 | Dwek et al. ................. 436/501 |

FOREIGN PATENT DOCUMENTS

| EP | 0 057 236 | | 8/1982 | .......... G01N/33/58 |
| WO | 7900256 | * | 5/1979 | |
| WO | WO8404169 | | 10/1984 | |
| WO | 8404169 | * | 10/1984 | |

OTHER PUBLICATIONS

Nahm Et Al. Journal of Clinical Microbiology Oct. 1980, P. 506–508 vol. 12, No. 4.*
Harris Et Al. In Clinics in Laboratory Medicine, Lee, W.S., ed., vol.5(3), W.B. Saunders Company, Philadelphia, pp. 545–560 (1985).*
Dellerich, M, J. Clin. Chem. Clin. Biochem., vol.22 (12), pp. 895–904 (1984).*
Sela et al., Proc. Natl. Acad. Sci. USA, vol.72(3), pp. 1127–1131 (Mar. 1975).*
Symington, et al., "Fine Specificity of a Monoclonal Antibody . . . ", *Molecular Immunology*, 21, 10, 877–882 (1984).
Chechik, et al., "Immunochemistry of Highly Branched N–Glycans . . . ", *Biochem. Cell. Biol.*, 66, 1333–1341 (1988).
Galili, et al., "The Human Natural Anti–Gal IgG III . . . ", *J. Exp. Med. vol.*, 165, 693–704 (1987).
R. B. Parekh, et al., "Association of Rheumatoid Arthritis and Primary Osteoarthritis with Changes in the Glycosylation Pattern of Total Serum IgG," *Nature*, 316(1), 452–457 (1985).
R. Lotan Et Al., Enhanced Glycosylation of a Melanoma Cell etc. Cancer Biochem Biophys., (Houston, Texas) 9(3) 211–221 01/87.
D. Russell Et Al., Glycosylation of Purified Enveloped etc. Virus Research, (Manhattan, Kansas) 4(1) 83–91 01/85.
D. Deane Et Al., Correlation Between Tumorigenicity and Altered etc. Int. J. Cancer, (Edinburgh, United Kingdom) 34(4) 459–462 01/84.
R. Parekh Et Al., Association of Rheumatoid Arthritis and etc. Nature, (Oxford, United Kingdom) 316 452–457 08/85.
M. Malaise Et Al., Increased Concanavalin A–Binding Capacity of etc. Clin. Exp. Immunol., (Liege, Belgium) 68(3) 543–551 01/87.

* cited by examiner

Primary Examiner—Yvonne Eyler
(74) Attorney, Agent, or Firm—Fitzpatrick, Cella, Harper & Scinto

(57) ABSTRACT

Monoclonal antibodies raised against cell walls of Group A Streptococci are specific to biological materials, e.g. immunoglobulins, having terminal N-acetylglucosamine residues and can be used in their detection, e.g. in the diagnosis of diseases characterized by their presence, e.g. rheumatoid arthritis and Crohn's disease.

14 Claims, No Drawings

MONOCLONAL ANTIBODIES AND THEIR PRODUCTION AND USE

This is a File Wrapper Continuation Application under 37 CFR §1.62 of application Ser. No. 07/892,394, filed May 28, 1992, now abandoned which is a File Wrapper Continuation Application under 37 CFR §1.62 of application Ser. No. 07/510,639, filed on Apr. 18, 1990, now abandoned, which is a Continuation Application under 37 CFR §1.60 of application Ser. No. 07/078,770, filed Jul. 28, 1987, now abandoned.

This invention relates to monoclonal antibodies and their production and use.

It has been reported that some patients with rheumatoid arthritis have raised levels of antibody to the polysaccharide/peptidoglycan complex of the cell walls of Group A Streptococci (Johnson et al, Clin. exp. Immunol., 55, 115 and 61, 373). It has also been reported that mice immunised with purified rheumatoid factor, i.e. immunoglobulin, from rheumatoid arthritis patients, develop antibodies to Group A Streptococci (Johnson et al, Clin. exp. Immunol., 61, 373).

It has recently been shown that the sugar residues on immunoglobulins taken from rheumatoid arthritis patients terminate with N-acetylglucosamine (GlcNAc) significantly more frequently than do normal immunoglobulins (Parekh et al, Nature, 316, 452). It is known that N-acetylglucosamine linked to polyrhamnose is a major determinant of Group A Streptococci.

We have discovered that the N-acetylglucosamine present in the cell walls of Group A Streptococci is in essentially the same configuration as the N-acetylglucosamine present in the abnormal immunoglobulins of patients with rheumatoid arthritis. Consequently, antibodies raised against the cell walls of Group A Streptococci are capable of binding to N-acetylglucosamine residues in biological materials, e.g. the abnormal immunoglobulins of rheumatoid arthritis patients and may be used in assay methods for the detection and estimation of such biological materials.

Using this discovery, we have now produced monoclonal antibodies to the cell walls of Group A Streptococci, or more specifically to the glycoproteins having terminal N-acetylglucosamine residues present therein. Such antibodies are specific to biological materials, eg. immunoglobulins, containing terminal N-acetylglucosamine residues. Murine hybridomas capable of producing such monoclonal antibodies also form part of the invention. Such monoclonal antibodies can be used in assay methods for the purposes described below. It is particularly advantageous to be able to produce antibodies to abnormal immunoglobulins using an antigen which is not the immunoglobulin itself, since the monoclonal antibodies of the present invention can be made highly specific for abnormal immunoglobulins containing terminal N-acetylglucosamine residues and without the ability to bind other parts of immunoglobulins.

The monoclonal antibodies of the invention may be produced in accordance with generally known techniques, see for example, "Monoclonal antibodies: production and maintenance" by U. Lovborg (1982). William Heinemann Medical Books, London. For example, mice are immunised with respect to Group A Streptococcal cell walls. The cell wall material is injected into the mice. Spleen cells from the mice are then fused with myeloma cells, e.g. of a mouse myeloma cell line. The hybridomas thus-produced are screened for those producing antibodies possessing the correct specificity. This may be achieved by screening the antibodies by enzyme-linked immunoabsorbent assay (ELISA) on bovine serum albumin conjugated to N-acetylglucosamine (BSA-N-AG), enzyme treated fetuin (ETF) and fetuin. Fetuin is a glycoprotein found in serum which contains N-acetylglucosamine normally hidden in its structure. Treatment with sialidase and galactosidase cleaves the molecule to expose the N-acetylglucosamine and give ETF. Hybridomas producing antibodies positive both to BSA-N-AG and ETF but negative to fetuin are kept.

The novel monoclonal antibodies to N-acetylglucosamine produced in accordance with the present invention have a variety of significant utilities. They can be used more particularly to detect and assay biological materials, i.e. materials of cellular origin, usually proteins, having exposed N-acetylglucosamine residues, e.g. abnormally glycosylated immunoglobulins in body fluids taken from patients suffering from, or suspected of suffering from, rheumatoid arthritis, tuberculosis, leprosy, Crohn's disease and similar diseases in experimental animals such as mice. The monoclonal antibodies of the invention provide an important way of detecting and estimating the presence of the abnormal immunoglobulins believed to be associated with such conditions.

The new monoclonal antibodies may also be used in the differentiation of certain types of tumour. There is evidence that tumours which bear terminal N-acetylglucosamine residues may be more susceptible to recognition by cells of the immune response, and may trigger release of cytotoxic molecules from such cells (Dennis et al, Eur. J. Biochem. (1986) 161:359–373). Receptors able to recognise GlcNAc appear to exist on myeloid cells (Ross et al., (1985), J. Immunol., 134:3307–3315; Haltiwanger & Hill, 1986, J. Biol. Chem., 261:7440–7444). A consequence of recognition of agalactosyl tumours by such cells may be a markedly reduced tendency of such tumours to metastasise. This has been demonstrated in a murine model by Dennis et al. The monoclonal antibodies of the invention can therefore be used on cancerous cells, e.g. from biopsy material, or tumours removed at surgery (e.g. in cancer of the breast), to predict the likely prognosis (i.e. their tendency to metastatize). The monoclonal antibodies of the invention do not bind to cell membranes on normal tissues, but they bind strongly to cell membranes of tumour cells having terminal N-acetylglucosamine residues on the surface, and when revealed by a suitable colour-forming label they give strong membrane staining on such cells. This has been demonstrated on a murine tumour (L929) which triggers its own destruction via cytotoxin release from macrophages which it contacts.

In clinical use, the monoclonal antibodies of the invention also make it possible to assay variations in. levels of abnormally glycosylated immunoglobulins. This assists in predicting the nature of acute abdominal crises in Crohn's disease; assessing the efficacy of treatment in rheumatoid arthritis; monitoring the effects of immunotherapy of bladder cancer using *Mycobacterium tuberculosis* (var BCG); monitoring correction by immunotherapy of the immunopathological mechanisms seen in tuberculosis. The new monoclonal antibodies may also be useful in veterinary practice, for example for screening badgers for tuberculosis. As is well known, wild badgers act as a reservoir of bovine tuberculosis from which domestic cattle can be infected. To prevent indiscriminate slaughter of badgers suspected of carrying bovine tuberculosis, a simple assay method is desirable, and the monoclonal antibodies of the present invention make this possible.

For these purposes, the novel monoclonal antibodies of the present invention may be used in, for example, enzyme-linked immunoassay in the same way as known monoclonal antibodies, but relying on the specific ability of the novel antibodies to bind with N-acetylglucosamine residues generally, and especially such residues present in immunoglobulin (IgG). Enzyme-linked immunoassay is a well known technique: reference may be made, for example, to Rook and Cameron, (1981), J. Immunological Methods, 40, 109–114. By making the new monoclonal antibodies from the cell walls of Group A Streptococci rather than from the abnormal immunoglobulin of rheumatoid arthritis patients, it is possible to achieve a much higher specificity of action for N-acetylglucosamine without interference from other affinities.

In general, the monoclonal antibodies of the invention may be used to detect and/or estimate biological materials having terminal N-acetylglucosamine residues by causing the said biological material to bind to the monoclonal antibody, and to a label under conditions such that the bound or unbound label provides a measure of the said biological material, and detecting or estimating the said bound or unbound label. The label may be any of the labels currently used in immuno-assay techniques including radioactive, fluorescent and enzyme labels. Preferably an enzyme label is used along with a colour forming reagent which undergoes a chromogenic reaction catalysed by the said enzyme.

Heterogeneous assay methods are usually preferred. The immunoglobulin or other biological material to be assayed is bound to a solid support, e.g. by adsorption to an appropriate surface, the monoclonal antibody is allowed to bind to the biological material on the solid support, a label is attached directly or indirectly to said monoclonal antibody, and the said label is then assayed.

Where the biological material is a mammalian cell, e.g. from a tumour under investigation for the reasons explained above, a separate solid support is not required and the monoclonal antibody is allowed to bind to the cell itself, i.e. to any terminal N-acetylglucosamine residues present on the surface of the said cell, the label is attached directly or indirectly to any bound monoclonal antibody and the label is then observed or assayed. Single cells can be examined under the microscope in this way.

Suitable enzyme labels include peroxidase, β-galactosidase, alkaline phosphatase, and glucose oxidase. In each case, a means for revealing or determining the bound enzyme label is provided in the form of a suitable substrate for the enzyme, e.g. a combination of hydrogen peroxide and a compound, e.g. o-phenylene diamine or 4-chloro-naphthol which produces a colour when oxidized by the hydrogen peroxide under the influence of the enzyme.

The label may be attached to the monoclonal antibody by an anti-mouse immunoglobulin covalently linked to the said label. Alternatively, and preferably, the monoclonal antibody of the invention is biotinylated in known manner and the label is bound thereto using avidin covalently linked to the said label.

The following Example illustrates the invention.

EXAMPLE

Balb/C mice were immunised by an intraperitoneal injection of 50 μg of Group A Streptococcal cell walls (Johnson et al., (1984) Clinical & Experimental Immunology, 55,115) emulsified in Freund's incomplete adjuvant. The injection was repeated three weeks later, and a further booster injection was given intravenously 4 days before the mice were killed. (The intravenous dose was in an oil/water emulsion containing 10 μg squalene/ml of phosphate buffered saline+ Tween 80). Spleen cells from the immunised mice were then fused with cells of the JK non-secreting mouse myeloma cell line (P3-X63-Ag 8, see Kearny et al (1979), J. Immunol. 123,1548). The hybridised cells were screened for production of the desired antibodies by enzyme-linked immunosorbent assay using the following antigens:

(1) Bovine serum albumin to which N-acetylglucosamine residues had been bound by coupling the bovine serum albumin with diazotised amino-phenyl N-acetylglucosamine (BSA-N-AG) (Zopf et al (1978) Archives of Biochemistry and Biophysics, 185,61–71); and (2) Fetuin which had been treated with Sialidase and Galactosidase so that N-acetylglucosamine became the terminal sugar (ETF). Fetuin was purified by passage through a 5 micron TSK-250 (21.5×600 mm) gel filtration chromatography column equilibrated in 0.1M potassium phosphate at pH 7.4. A fraction of HPLC purified fetuin (10 mg/ml) was subsequently incubated for 24 hours at 37° C. under toluene with 10 units/ml of neuraminidase (sialidase) from *Arthrobacter ureafaciens* (from Boehringer Mannheim), and Jack Bean β-galactosidase (purified from Jack-Bean meal as described by R. Parekh, D. Phil, Thesis, Oxford, 1987 based on Lee & Lee, "Methods in Enzymology", (1972) 28, 702–713) in 0.1M sodium citrate at pH 4.0. The asialoagalacto-fetuin was finally purified by gel filtration chromatography as described above.

The most active cell lines identified by these methods were then further screened using immunoglobulin known to show raised levels of N-acetylglucosamine. For this purpose the abnormal immunoglobulin was denatured in 12 molar urea solution with 0.5 molar 2-mercaptoethanol at 40° C. for 16 hours followed by dialysis against iodoacetamide to block the liberated mercapto groups. This treatment results in complete unwinding of the immunoglobulin chains and enhances exposure of the sugar residues. The denatured immunoglobulin obtained in this way was coated onto the polystyrene walls of a microtitre plate at a concentration of 10 μg/ml in a carbonate/bicarbonate buffer. For control purposes other wells in the microtitre plate were coated with the same amount of known normal immunoglobulin. Monoclonal antibody from a selected cell line, diluted in phosphate-buffered saline containing 0.05% of Tween 20, was incubated in the immunoglobulin-coated wells of the microtitre plate. The quantity of bound monoclonal antibody was then assayed by adding peroxidase-conjugated rabbit anti-mouse IgG followed by the enzyme substrate and chromogen. To check that the test and control cells contained equal quantities of immunoglobulin, anti-human IgG was added to some of the immunoglobulin-coated wells so that total bound immunoglobulin could be estimated.

In this way, six hybridomas producing monoclonal antibody positive both to BSA-N-AG and to ETF but negative to fetuin were located. Of these, two were chosen which had the greatest ratio of binding to ETF compared with the background binding to fetuin one of which has since been designated GN7, and was accepted for deposit by the European Collection of Animal Cell Cultures, PHLS Centre for Applied Microbiology and Research, Porton Down, Salisbury, Wiltshire SP4 OJG, United Kingdom, under the terms and conditions of the Budapest Treaty of 1977 on Apr. 30, 1992, and has been accorded accession number 92043039.

This method for screening the mouse cell lines may be adapted to use the monoclonal antibodies of the invention in immunoassay. The immunoglobulin to be determined, e.g. in a serum sample taken from a patient, is coated in an appropriate dilution onto the walls of a microtitre plate made of polystyrene or other polymer capable of binding proteins. The monoclonal antibody of the invention is incubated in the immunoglobulin-coated wells of the microtitre plate. Peroxidase-conjugated rabbit anti-mouse IgG is then added to each well followed by the enzyme substrate (hydrogen peroxide) and chromogen (e.g. o-phenylenediamine). The colour produced depends on the amount of bound enzyme which itself depends on the amount of immunoglobulin in the initial sample having free N-acetylglucosamine residues and therefore capable of binding the monoclonal antibodies of the invention.

Preferably, however, an assay using the novel monoclonal antibodies is carried out as follows: All the operations are performed at room temperature. The biological material which may have terminal N-acetylglucosamine residues in a sample to be assayed is adsorbed onto nitrocellulose sheets. The high affinity of the biological material, which is proteinaceous, for this material (which does not bind sugars) results in enhanced exposure of any sugar residues that are present. In the first stage, 0.5 µg of each sample of biological material (previously purified, eg. by adsorption on protein A in the case of IgG) in 5 µl of phosphate buffered saline is spotted onto nitrocellulose. Conditions are controlled so that the size and concentration of each spot are kept constant. After drying for one hour, the nitrocellulose is boiled for 5 minutes. This further enhances exposure of the sugar residues and eliminates non-specific effects caused by rheumatoid factor activity, or any other antibody activity in the sample. The nitrocellulose is then incubated in 1% bovine serum albumin in phosphate buffered saline at pH 7.0 containing 0.05% Tween 20 (PBS/BSA/Tween) to block any other protein-binding sites.

The number of terminal GlcNAc's on each sample spot is then revealed by determining quantitatively the binding of the monoclonal antibody. To do this the monoclonal is biotinylated in known manner, e.g. by incubation overnight in phosphate-buffered saline of pH 7.0 containing N-hydroxy-succinimidobiotin (Sigma, catalogue number 11-1759). Conjugation occurs spontaneously. The nitrocellulose is then incubated in biotinylated monoclonal (diluted 1:2000 in PBS/BSA/Tween™), and then an avidin-peroxidase complex (from Amersham International plc, GB; diluted 1:500 in PBS/BSA/Tween™; Yolken et al, J. Immunol Methods (1983), 56, 319–327), and finally hydrogen peroxide and 4-chloronaphthol, are added. This results in blue spots the intensity of which is related to the amount of terminal GlcNAc's present in the sample.

The blue spots are measured by sandwiching the nitrocellulose between a red light emitting diode and a photodiode, linked to a suitable amplifier. The apparatus (based on that described by Rook and Cameron (1981), J. Immunological Methods 40, 109–114) can be calibrated using samples of IgG of known terminal N-acetylglucosamine content.

In an alternative procedure, protein A or protein G is first adsorbed into the nitrocellulose, eg. by incubation of the latter in 100 µg/ml protein A in phosphate-buffered saline (PBS) for two hours. Then remaining protein-binding sites are blocked by incubation overnight in PBS/BSA/Tween 20. Then the nitrocellulose bearing the protein A is incubated in serum diluted 1:2 in PBS for two hours, in order to saturate the IgG-binding sites on the protein A with IgG. Then it is washed 4 times in PBS, and fixed in 0.5% glutaraldehyde (Electron microscopy grade) in PBS for 30 minutes at 4° C. to ensure permanent binding of the IgG to the protein A. Then the nitrocellulose now bearing both protein A and IgG bound to the protein A, is incubated in (0.1 molar lysine in PBS to block remaining aldehyde groups.

Then the nitrocellulose is dried, boiled, and treated exactly as for the nitrocellulose-based assay described above.

What is claimed is:

1. A hybridoma which is capable of producing a monoclonal antibody which:
   (i) has been raised against the cell walls of Group A Streptococci; and
   (ii) is specific to mammalian cells or membranes, or mammalian immunoglobulins of the IgG class, containing terminal N-acetylglucosamine residues;

wherein, in an enzyme-linked immunoabsorbent assay, said monoclonal antibody is:
   (i) negative to fetuin; and
   (ii) positive to:
      (a) bovine serum albumin conjugated to N-acetylglucosamine residues;
      (b) fetuin which has been treated with sialidase and galactosidase; and
      (c) immunoglobulins which have been denatured.

2. The hybridoma of claim 1 which is a murine hybridoma.

3. The hybridoma of claim 2 which has been produced by the fusion of a murine myeloma cell with an antibody-producing spleen cell obtained from a mouse which has been immunized with Group A Streptococci cell walls.

4. The hybridoma of claim 3 which has been deposited with the European Collection of Animal Cell Cultures under Accession Number 92043039.

5. A monoclonal antibody which:
   (i) has been raised against the cell walls of Group A Streptococci; and
   (ii) is specific to mammalian cells or membranes, or mammalian immunoglobulins of the IgG class, containing terminal N-acetylglucosamine residues;

wherein, in an enzyme-linked immunoabsorbent assay, said monoclonal antibody is:
   (i) negative to fetuin; and
   (ii) positive to:
      (a) bovine serum albumin conjugated to N-acetylglucosamine residues;
      (b) fetuin which has been treated with sialidase and galactosidase; and
      (c) immunoglobulins which have been denatured.

6. The monoclonal antibody of claim 5 which is produced by a murine hybridoma.

7. The monoclonal antibody of claim 6 wherein said hybridoma has been produced by the fusion of a murine myeloma cell with an antibody-producing spleen cell obtained from a mouse which has been immunized with Group A Streptococci cell walls.

8. The monoclonal antibody of claim 7 wherein said hybridoma is the hybridoma which has been deposited with the European Collection of Animal Cell Cultures under Accession Number 92043039.

9. A method for producing a hybridoma which produces a monoclonal antibody which:
   (i) has been raised against the cell walls of Group A Streptococci, and (ii) is specific to mammalian cells or membranes, or mammalian immunoglobulins of the IgG class, containing terminal N-acetylglucosamine residues, comprising:

(a) immunizing a mammal with the cell walls of Group A Streptococci;

(b) recovering spleen cells from said mammal;

(c) fusing said spleen cells with myeloma cells to produce hybridomas; and (d) screening said hybridomas to select those which produce a monoclonal antibody which is specific to mammalian cells or membranes, or mammalian immunoglobulins of the IgG class, containing terminal N-acetylglucosamine residues;

wherein, in an enzyme-linked immunoabsorbent assay, said monoclonal antibody is:

(i) negative to fetuin; and (ii) positive to:

(a) bovine serum albumin conjugated to N-acetylglucosamine residues;

(b) fetuin which has been treated with sialidase and galactosidase; and (c) immunoglobulins which have been denatured.

10. The method of claim 9 wherein said spleen cells and said myeloma cells are both murine cells.

11. The method of claim 10 wherein the hybridoma produced is equivalent to the hybridoma which has been deposited with the European Collection of Animal Cell Cultures under Accession Number 92043039.

12. A method for producing a monoclonal antibody which:

(i) has been raised against the cell walls of Group A Streptococci, and (ii) is specific to mammalian cells or membranes, or mammalian immunoglobulins of the IgG class, containing terminal N-acetylglucosamine residues, comprising:

(a) immunizing a mammal with the cell walls of Group A Streptococci;

(b) recovering spleen cells from said mammal;

(c) fusing said spleen cells with myeloma cells to produce hybridomas; and (d) screening said hybridomas to select those which produce a monoclonal antibody which is specific to mammalian cells or membranes, or mammalian immunoglobulins of the IgG class, containing terminal N-acetylglucosamine residues; and (e) producing said monoclonal antibody;

wherein, in an enzyme-linked immunoabsorbent assay, said monoclonal antibody is:

(i) negative to fetuin; and (ii) positive to:

(a) bovine serum albumin conjugated to N-acetylglucosamine residues;

(b) fetuin which has been treated with sialidase and galactosidase; and (c) immunoglobulins which have been denatured.

13. The method of claim 12 wherein said spleen cells and said myeloma cells are both murine cells.

14. The method of claim 13 wherein the hybridoma produced is equivalent to the hybridoma which has been deposited with the European Collection of Animal Cell Cultures under Accession Number 92043039.

* * * * *